(12) United States Patent
Nivorozhkin

(10) Patent No.: US 11,098,024 B2
(45) Date of Patent: Aug. 24, 2021

(54) METHODS AND RELATED TOOLS FOR CBD CONVERSION TO THC

(71) Applicant: Alex Nivorozhkin, West Roxbury, MA (US)

(72) Inventor: Alex Nivorozhkin, West Roxbury, MA (US)

(73) Assignee: ARIELIUM HEALTH, LLC, West Roxbury, MA (US)

( * ) Notice: Subject to any disclaimer, the term of this patent is extended or adjusted under 35 U.S.C. 154(b) by 0 days.

(21) Appl. No.: 16/741,741

(22) Filed: Jan. 13, 2020

(65) Prior Publication Data

US 2020/0223814 A1    Jul. 16, 2020

Related U.S. Application Data

(60) Provisional application No. 62/791,122, filed on Jan. 11, 2019.

(51) Int. Cl.
| | | |
|---|---|---|
| *C07D 311/80* | (2006.01) | |
| *B01J 8/02* | (2006.01) | |
| *B01J 8/00* | (2006.01) | |
| *B01J 31/10* | (2006.01) | |
| *B01J 21/08* | (2006.01) | |
| *B01J 27/12* | (2006.01) | |
| *B01J 29/08* | (2006.01) | |
| *B01J 29/85* | (2006.01) | |
| *B01J 35/02* | (2006.01) | |
| *A61M 11/04* | (2006.01) | |
| *A24F 40/40* | (2020.01) | |
| *B01J 29/40* | (2006.01) | |

(52) U.S. Cl.
CPC ............ *C07D 311/80* (2013.01); *A24F 40/40* (2020.01); *A61M 11/041* (2013.01); *B01J 8/001* (2013.01); *B01J 8/0285* (2013.01); *B01J 21/08* (2013.01); *B01J 27/12* (2013.01); *B01J 29/08* (2013.01); *B01J 29/40* (2013.01); *B01J 29/85* (2013.01); *B01J 31/10* (2013.01); *B01J 35/026* (2013.01); *B01J 2208/00212* (2013.01); *B01J 2208/00628* (2013.01)

(58) Field of Classification Search
CPC .................................................... C07D 311/80
See application file for complete search history.

(56) References Cited

U.S. PATENT DOCUMENTS

| | | |
|---|---|---|
| 2004/0049059 A1 | 3/2004 | Mueller |
| 2010/0210860 A1* | 8/2010 | Erler .................... C07D 311/80 549/390 |
| 2016/0211693 A1 | 7/2016 | Stevens et al. |

\* cited by examiner

*Primary Examiner* — John S Kenyon
(74) *Attorney, Agent, or Firm* — JWIP & Patent Services, LLC; Jacob G. Weintraub, Esq.

(57) ABSTRACT

The present invention is directed to methods of producing THC from CBD utilizing non-harsh methodology and resulting in substantially increased yields, as well as devices built upon these novel methods. The methods and devices are material efficient, and in certain embodiments, solvent-free. In particular, in certain embodiments, these methods and related devices are suitable for commercial production of THC from CBD. Furthermore, in certain embodiments, the present invention provides methods of producing THC from CBD in manner that affords tunability to select the ratio of THC-8 to THC-9.

20 Claims, 1 Drawing Sheet

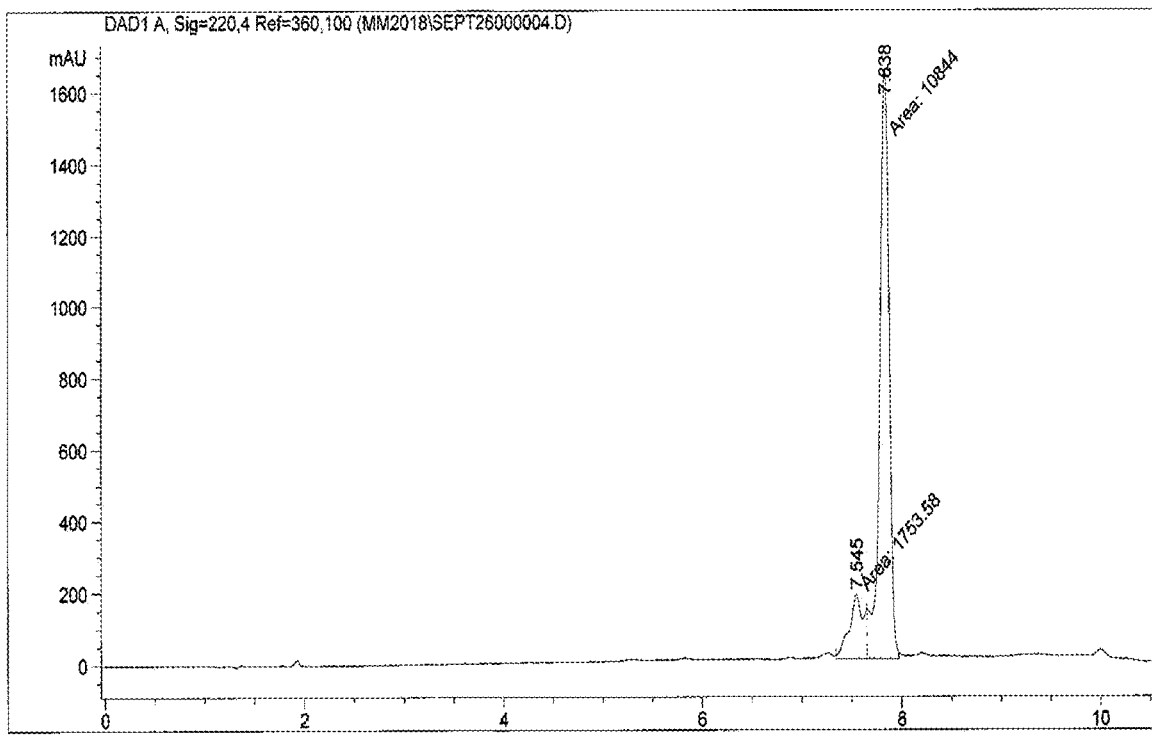
Panel A
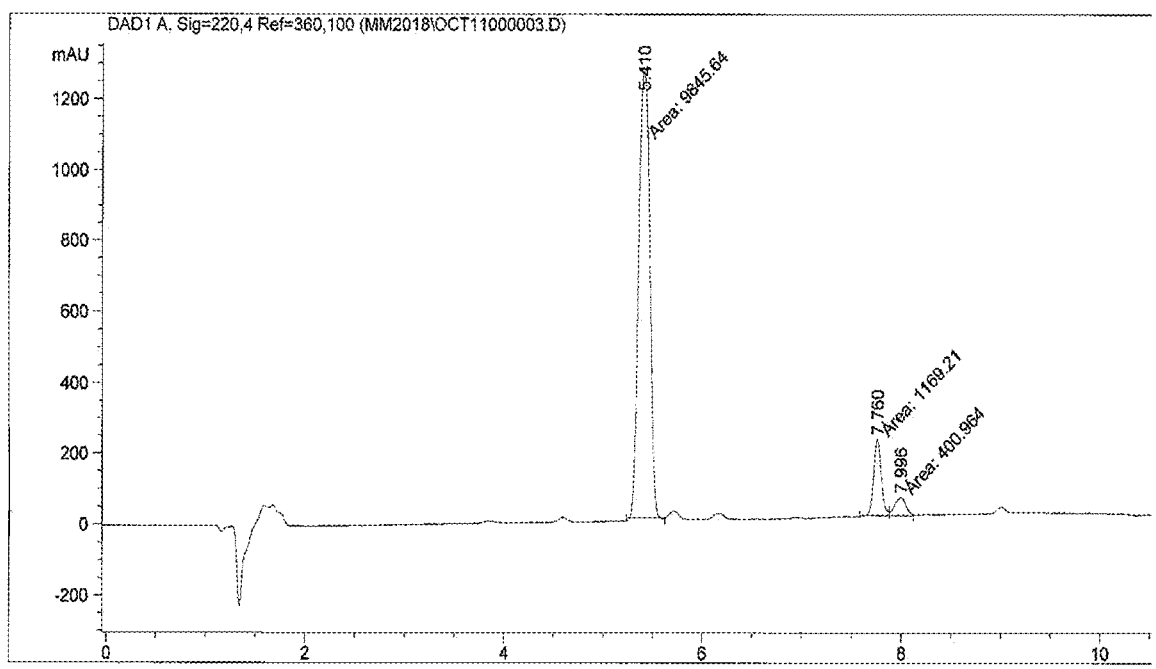
Panel B

METHODS AND RELATED TOOLS FOR CBD CONVERSION TO THC

RELATED APPLICATIONS

This application claims priority to U.S. Provisional Patent Application No. 62/791,122, filed on Jan. 11, 2019; the entirety of which is incorporated herein by reference.

BACKGROUND OF THE INVENTION

The predominantly occurring cannabinoids in *cannabis* plant material, commonly referred to as tetrahydrocannabinol ("THC") and cannabidiol ("CBD"), are in fact (−)-trans-$\Delta^9$-THC and (−)-trans-$\Delta^1$-CBD. In addition, (−)-trans-$\Delta^8$-THC is also routinely detected in plant isolates, though in small quantities, and is oft subsumed within the category of THC. Such naturally occurring compounds have been suggested for use in treatment of an ever-growing list of medical conditions, including epilepsy, pain, inflammation, anxiety reduction, sleep improvement, multiple sclerosis, neuropathic pain, spasticity, overactive bladder, antiemesis, and appetite stimulation. Others have found these compounds to be indicated for recreational use related to certain of their psychoactive properties. In either case, these compounds have become of major pharmacological interest in the last 20 years.

However, despite significant recent advances in synthetic chemistry of cannabinoids and the availability of CBD produced by the plant, e.g., particularly in genetically modified *cannabis* plant material, very little development has taken place in the advancement in the production of commercially relevant quantities of THC from CBD. In fact, known synthetic processes to produce THC that have been developed have required harsh reagents, including use of BrØnsted or Lewis acids and solvation conditions, not suitable for large scale commercial production. Moreover, in many cases the processes for THC synthesis have, at best, resulted in low yields of THC, making use of these synthetic schemes cost prohibitive. Given this lack of success in chemical synthesis of THC, commercial production of THC has been generally relegated to enhancements of isolation techniques and plant based engineering for extraction of the natural product.

As such, there remains a need for methods of producing THC from CBD that utilize non-harsh methodology with increased yields, particularly in a manner suitable for commercial production.

SUMMARY OF THE INVENTION

Accordingly, the present invention is directed to methods of producing THC from CBD utilizing non-harsh methodology and resulting in substantially increased yields, as well as devices built upon these novel methods. The methods and devices are material efficient, and in certain embodiments, solvent-free. In particular, in certain embodiments, these methods and related devices are suitable for commercial production of THC from CBD. Furthermore, in certain embodiments, the present invention provides methods of producing THC from CBD in manner that affords tunability to select the ratio of THC-8 to THC-9.

As such, one aspect of the present invention provides a material-efficient method for conversion of cannabidiol (CBD) to tetrahydrocannabinol (THC). The method comprises the step of: introducing CBD to acidicly enriched solid support particles to create a CBD-activated accelerated conversion environment, such that THC is produced.

Another aspect of the present invention provides a tunable material-efficient method for conversion of cannabidiol (CBD) to tetrahydrocannabinol (THC). The method comprises the step of: introducing CBD to acidicly enriched solid support particles to create a CBD-activated accelerated conversion environment, such that THC is selectively produced in the accelerated conversion environment.

Another aspect of the present invention provides a solvent-free method for conversion of cannabidiol (CBD) to tetrahydrocannabinol (THC) comprising the step of: introducing CBD to acidicly enriched solid support particles through direct melt of the CBD to create a CBD-activated accelerated conversion environment, such that THC is produced.

Yet another aspect of the present invention provides a tetrahydrocannabinol (THC) production device comprising: a vessel for containing acidicly enriched solid support particles; and a plurality of CBD-activated acidicly enriched solid support particles positioned inside the vessel, wherein THC is produced from the CBD-activated acidicly enriched solid support particles.

Still yet another aspect of the present invention provides a tunable tetrahydrocannabinol (THC) production device comprising: a vessel for containing acidicly enriched solid support particles; and a plurality of acidicly enriched solid support particles positioned inside the vessel, wherein THC is produced from the CBD-activated acidicly enriched solid support particles.

Another aspect of the present invention provides a tetrahydrocannabinol (THC) production personal use device comprising a vessel for containing acidicly enriched solid support particles, wherein the vessel is designed for personal use; and a plurality of acidicly enriched solid support particles positioned inside the vessel, wherein THC is produced from the CBD-activated acidicly enriched solid support particles.

BRIEF DESCRIPTION OF THE FIGURES

Advantages of the present methods and related devices will be apparent from the following detailed description, which description should be considered in combination with the accompanying figures, which are not intended to limit the scope of the invention in any way.

FIG. 1 depicts an (A) HPLC trace of the reaction product from the Amberlyst-15-catalyzed CBD to THC transformation (heptane, reflux 45 min); and (B) HPLC trace of the reaction mixture from the Amberlyst-15-catalyzed CBD to THC transformation (heptane, ambient temperature, 2 h). The peak assignment as following: CBD (RT 5.41 min), (−)$\Delta^9$-THC (RT 7.76 min), (−)$\Delta^8$-THC (RT 7.99 min).

DETAILED DESCRIPTION OF THE INVENTION

The present invention is directed to methods and related devices for use in conversion of cannabidiol (CBD) (e.g., and simple derivatives thereof) to tetrahydrocannabinol (THC) (e.g., and simple derivatives thereof). Both CBD and THC have two carbon stereo-centers that give rise to four diastereomers, (−)-cis-, (+)-cis-, (−)-trans-, and (+)-cis-. The nature-selected ones, and more potent psychoactive compounds, are those with (−)-trans-configuration. In this respect, the chemical structures of CBD and THC are as follows:

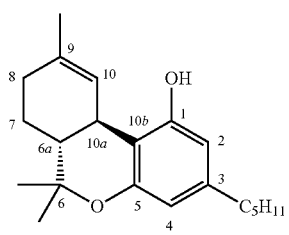

(−)-trans-$\Delta^9$-THC

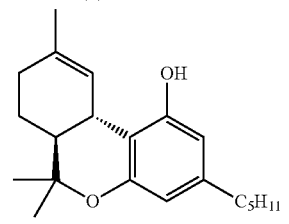

(+)-trans-$\Delta^9$-THC

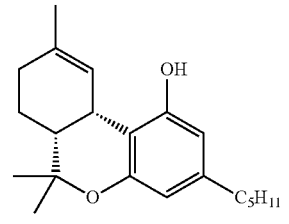

(−)-cis-$\Delta^9$-THC

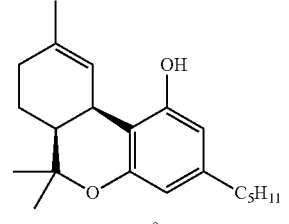

(+)-cis-$\Delta^9$-THC

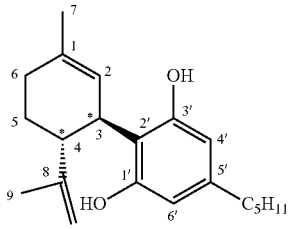

(−)-trans-(3R,4R)-CBD

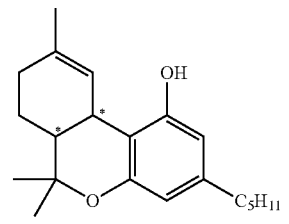

$\Delta^8$-THC

Positional isomerization of the vinyl group in the CBD carbocycle leads to $\Delta^9$-, $\Delta^8$- for THC, where the $\Delta^8$-THC is putatively regarded as thermodynamically more stable than $\Delta^9$-THC. Moreover, for convenience, $\Delta^9$-THC is referred to herein as THC-9, and $\Delta^8$-THC is referred to herein as THC-8.

Cyclization of CBD to THC has previously been reported to be catalyzed by both Lewis and BrØnsted acids. However, historically such conversion has required harsh solvent conditions (such as toluene) and reagents (such as $BF_3$-$Et_2O$) that entail separation/removal from the reactions products (e.g., in certain circumstances, difficult separation/removal) after the solution phase conversion. In many cases, beyond the inefficiency with respect to material, the results of this solution phase conversion after standard workups (and further chromatographic separation) were poor yields, at best. The lack of commercial utility may be evidenced by the lack of any known commercial production of THC from CBD.

Accordingly, the present invention utilizes acidicly enriched solid support particles with no additional catalytic molecules, e.g., no additional acidic catalytic agents in the methods and devices of the present invention, beyond the acidicly enriched solid support particles (no further acid added to reaction other than solid support is required for conversion). The method utilizes the introduction of CBD to the acidicly enriched solid support particles to create a CBD-activated accelerated conversion environment in order to convert the CBD to THC in a one-step process.

In certain embodiments, the resulting THC is therefore produced from the one step conversion and the product isolation is achieved simply by a removal of the solid support particles. The process and related devices avoid harsh solvent conditions and are completed within a substantially reduced time frame (e.g., compressed time frame), producing high levels of conversion of CBD (i.e., the conversion reactions go to completion or near completion) with very clean crude reaction product, including low (to no) residual solvent contamination. The processes and devices of the present invention of the invention are therefore material efficient and commercially relevant.

The increased rates of reaction afford the devices of the present invention the ability to take numerous convenient forms, e.g., commercially convenient, including those that afford flow adaptions to CBD isolation systems. Through the selection of the acidicly enriched solid support particles, selecting temperature, selecting time of reaction before extraction, and/or selecting a particular solvent, the THC ratio (i.e., between THC-9 and THC-8) may be selectively produced in the final conversion product. In particular, this ratio may be selectively produced as a single product or ratio of multiple products, e.g., including starting material CBD).

As such, the present invention is directed to methods of producing THC from CBD utilizing non-harsh methodology and resulting in substantially increased yields, as well as devices built upon these novel methods. The methods and devices are material efficient, and in certain embodiments, solvent-free. In particular, in certain embodiments, these methods and related devices are suitable for commercial production of THC from CBD. Furthermore, in certain embodiments, the present invention provides methods of producing THC from CBD in manner that affords tunability to select the ratio of THC-8 to THC-9.

The present invention, including devices and methods will be described with reference to the following definitions that, for convenience, are set forth below. Unless otherwise specified, the below terms used herein are defined as follows:

I. Definitions

As used herein, the term "a," "an," "the" and similar terms used in the context of the present invention (especially in the context of the claims) are to be construed to cover both the singular and plural unless otherwise indicated herein or clearly contradicted by the context.

The language "and/or" is used herein to mean both "and" in the conjunctive form and "or" in the disjunctive form.

The language "accelerated conversion environment" is used herein to describe the reaction environment that enhances and accelerates conversion of the CBD to THC created by the use of the acidicly enriched solid support particles of the present invention. Such enhancement and acceleration is relative to existing solution phase chemistry conversion of CBD to THC, and includes, for example, enhanced conversion efficiency of CBD, increased purity, e.g., of crude reaction, increased rate of production of THC, increased yield of production of THC, any combination thereof.

The language "acidicly enriched" as used in the language "acidicly enriched solid support particles" is used herein to describe the functionalization of the solid support particles of the present invention, i.e., the functional groups that are covalently linked to the support particles. Such functional groups must be suitable to achieve residual level acidity (i.e., comprising suitable Lewis or BrØnsted acid functional groups) to support the acidic catalysis of a reaction, i.e., the conversion of CBD to THC. This residual level of acidity is a characteristic of the functional groups covalently bound to the solid support particles, and is distinct from the addition of solution phase acid, e.g., in situ or in a pre-conditioning step.

The language "CBD-activated" is used herein to describe the presence of CBD, wherein the CBD has been introduced into or onto a material, e.g., on the acidicly enriched solid support particles of the present invention affording a CBD-activated accelerated conversion environment.

The term "introduce" or "introducing" is used herein to describe the non-covalent addition of one material, e.g., CBD, to another material, e.g., solid support particles.

The language "material-efficient" is used herein to describe methods/processes that reduce reaction conditions/reagents to reduce waste (as compared to existing methods/processes or in an absolute fashion when certain conditions/reagents are eliminated entirely), and therefore afford commercially relevant methods/devices such as those provided in the present invention. For example, in the present invention the use of the acidicly enriched support particles eliminates the need for harsh solvents and solution based acid catalysts, and are therefore material-efficient.

The language "reduced time frame" is used herein to describe the reduction in the time window in which a reaction proceeds, e.g., the CBD to THC conversion, as compared to existing/known reactions. In certain embodiments, the reduced time frame is a "compressed time frame" that describes a reaction that is complete within 1 min to 3 hours, e.g., 1 min to 2 hours, e.g., 1 min to 1 hours, e.g., 1 min to 30 min, e.g., 1 min to 20 min, e.g., 1 min to 15 min, e.g., 1 min to 10 min, e.g., 1 min to 5 min, e.g., less than 5 min.

The language "solid support particles" is used herein to describe solid particles used for non-covalent reaction support. The present invention utilizes solid support particles that are acidicly enriched. In particular embodiments, the acidicly enriched support particles are selected from the group consisting of acidicly enriched resin beads (e.g., Amberlyst-15 resin beads, Nafion particles), acidicly enriched functionalized silica gel (e.g., silica supported sulfonic and phosphoric acids), acidicly enriched zirconium oxide, acidicly enriched aluminosilicate zeolites, acidicly enriched aluminophosposilicate zeolites, and any combination thereof.

The term "tetrahydrocannabinol" or "THC" is art-recognized, and comprises all isomers, e.g., double bond isomers, unless otherwise stated.

The term "THC-9" is used herein as a representative notation for $\Delta^9$-THC" or "THC-delta-9."

The term "THC-8" is used herein as a representative notation for $\Delta^8$-THC" or "THC-delta-8." This isoform has been found to be close in potency (at the cannabinoid CB1 and CB2 receptors and in human clinical trials) to (−)-trans-$\Delta^9$-THC (Hollister, 1974; Hanus, 2016).

The term "tunable" is used herein to describe the ability to tune to, or select, a given product or product ratio by selecting additional factors for the method used or method-reliant device, such as, for example, selecting the acidicly enriched solid support particles, selecting the temperature, selecting the time of reaction before extraction, selecting the particular solvent, or any combination thereof.

The term "zeolite," as used in the present invention to describe solid support particles of the present invention comprising any member of the family of hydrated aluminosilicate minerals that contain alkali and alkaline-earth metals. In certain embodiments, the zeolites have a well-known three-dimensional tetrahedral framework structure wherein each oxygen atom is shared by two tetrahedral, and which encloses interconnected cavities, e.g., having diameters ranging from about 2 to 8 angstroms, typically occupied by large metal cations (positively charged ions) and water molecules. In fact, in naturally occurring zeolites, these metal ions are typically mono- or di-valent ions such as sodium, potassium, magnesium, calcium, and barium. However, the acidicly enriched solid support particles utilized in the methods and devices of the present invention are functionalized with hydrogen in replacement of these metal cations suitably to achieve residual level acidity.

II. Methods of the Invention for Conversion of CBD to THC

In accordance with the methods of the present invention, CBD may converted into THC by introduction to support particles that are acidicly enriched. The introduction of the CBD to the acidicly enriched solid support particles creates a CBD-activated accelerated conversion environment. In certain embodiments, the CBD may comprise additional functional groups in accordance with the well-known cannabinoid art, i.e., simple derivatives, which in turn may produce simple derivatives of THC as the final product rather than THC. The methods are material-efficient, tunable, and may be solvent-free in certain embodiments.

As such, one embodiment of the present invention provides a material-efficient method for conversion of cannabidiol (CBD) (e.g., and simple derivatives thereof) to tetrahydrocannabinol (THC) (e.g., and simple derivatives thereof) comprising the step of:
introducing CBD to acidicly enriched solid support particles to create a CBD-activated accelerated conversion environment, such that THC and simple derivatives thereof) is produced.

Another embodiment of the present invention provides a tunable material-efficient method for conversion of cannabidiol (CBD) (e.g., and simple derivatives thereof) to tetrahydrocannabinol (THC) (e.g., and simple derivatives thereof) comprising the step of:
introducing CBD to acidicly enriched solid support particles to create a CBD-activated accelerated conversion environment,
such that THC (e.g., and simple derivatives thereof) is selectively produced in the accelerated conversion environment (e.g., by selecting the acidicly enriched solid support particles, selecting temperature, selecting time of reaction before extraction). In certain embodiments, the THC (e.g., and simple derivatives thereof) is selectively produced as a single product or ratio of multiple products, e.g., including starting material CBD.

Yet another embodiment of the present invention provides a solvent-free method for conversion of cannabidiol (CBD) (e.g., and simple derivatives thereof) to tetrahydrocannabinol (THC) (e.g., and simple derivatives thereof) comprising the step of:

introducing CBD to acidicly enriched solid support particles through direct melt of the CBD to create a CBD-activated accelerated conversion environment, such that THC (e.g., and simple derivatives thereof) is produced.

Another embodiment of the present invention provides a material-efficient method for conversion of THC-9 (e.g., and simple derivatives thereof) to THC-8 (e.g., and simple derivatives thereof) comprising the step of:

introducing THC-9 to acidicly enriched solid support particles to create a THC-9-activated accelerated conversion environment, such that THC-8 (e.g., and simple derivatives thereof) is produced.

Certain embodiments of the methods of present invention further comprise the step of heating said CBD-activated accelerated conversion environment.

In certain embodiments of the present invention, the accelerated conversion environment is heated to less than or equal to 100° C.

In certain embodiments of the present invention, the acidicly enriched solid support particles are used less than 50%, e.g., less than 40%, e.g., less than 30%, e.g., less than 20%, e.g., less than 10%, by weight ratio with respect to the CBD.

In certain embodiments of the present invention, the acidicly enriched solid support particles are used in at least 10% by weight ratio with respect to the CBD.

In certain embodiments of the methods of present invention, the step of introducing the CBD to the acidicly enriched solid support particles is through solvent dissolution (e.g., using a hydrocarbon solvent or an oil, e.g., natural or synthetic) of the CBD to create the CBD-activated accelerated conversion environment. In certain embodiments, the solvent may be recovered following conversion, supporting a more renewable "green" process. In certain embodiments, the isolation/separation of the THC produced may be achieved by separation of the reaction solvent from the acidicly enriched solid support particles, e.g., without additional reaction workup. In particular embodiments, this separation may be through additional solvent extraction, e.g., solvent washing of the particles to recover THC produced.

In certain embodiments of the methods of present invention, the step of introducing the CBD to the acidicly enriched solid support particles is through solvent-free direct melt of the CBD to create the CBD-activated accelerated conversion environment. In certain embodiments, the acidicly enriched solid support particles are used at a 50% by weight ratio with respect to the CBD. Such direct melt processing capitalizes on the low melting point of CBD (m.p. 66° C.) and occurrence of THC as oil. In certain embodiments, the acidicly enriched solid support particles also serve as a filtration/separation mechanism, i.e., THC impurities/side-products remain behind after solvent washing of the particles to recover the THC produced in the melt on the particles. In particular embodiments, THC produced is greater than 90% pure THC. In specific embodiments, the solvent-free melt method increases the reaction speed as compared with non-melt (solvent based) conditions.

Certain embodiments of the methods of present invention further comprise the step of extraction of the solid support particles (e.g., using an appropriate solvent, e.g., a hydrocarbon solvent, an alcohol, or a plant oil).

In certain embodiments of the present invention, the THC produced in the accelerated conversion environment is selected from the group consisting of THC-9, THC-8, and any combination or ratio thereof.

In certain embodiments of the present invention, the THC is tunable, or selectively produced in the accelerated conversion environment. In certain embodiments, the selectivity is the result of selecting the acidicly enriched solid support particles, selecting temperature, selecting time of reaction before extraction, selecting a particular solvent, or any combination thereof. In particular embodiments, the selectively is produced as a single product or ratio of multiple products, e.g., including starting material CBD. In specific embodiments, the THC produced in the accelerated conversion environment has a THC-9 bias (e.g., greater than 50%, e.g., greater than 60%, e.g., greater than 70%, e.g., greater than 80%, e.g., greater than 90%). In alternative specific embodiments, the THC produced in the accelerated conversion environment has a THC-8 bias (e.g., greater than 50%, e.g., greater than 60%, e.g., greater than 70%, e.g., greater than 80%, e.g., greater than 90%).

In certain embodiments of the present invention, the THC produced in the accelerated conversion environment is produced with enhanced conversion efficiency of the CBD (i.e., consumption of CBD) with greater than 75% efficiency (e.g., greater than 80% efficiency, e.g., greater than 85% efficiency, e.g., greater than 90% efficiency, e.g., greater than 95% efficiency).

In certain embodiments of the present invention, the THC produced in the accelerated conversion environment (e.g., crude) is greater than 50% pure (e.g., greater than 60% pure, e.g., greater than 70% pure, e.g., greater than 75% pure).

In certain embodiments of the present invention, the THC produced in the accelerated conversion environment (e.g., crude) is greater than 80% pure (e.g., greater than 85% pure, e.g., greater than 90% pure, e.g., greater than 95% pure).

In certain embodiments of the present invention, the THC produced in the accelerated conversion environment is produced at an enhanced rate (e.g., less than or equal to 3 hours, e.g., less than or equal to 2 hours, less than or equal to 1 hour, e.g., less than or equal to 45 min, e.g., less than or equal to 30 min, e.g., less than or equal to 20 min, e.g., less than or equal to 15 min, e.g., less than or equal to 10 min, e.g., less than or equal to 5 min).

In certain embodiments of the present invention, the THC produced in the accelerated conversion environment is 50 g or greater (e.g., 100 g or greater, e.g., 250 g or greater).

In certain embodiments of the present invention, the THC produced in the accelerated conversion environment is 500 g or greater (e.g., 1 kg or greater, e.g., 5 kg or greater, e.g., 10 kg or greater, e.g., 20 kg or greater, e.g., 100 kg or greater, e.g., 500 kg or greater).

i. Solid Support Particles

In certain embodiments of the present invention, the solid support particles are selected from the group consisting of acidicly enriched polymer resin beads (e.g., Amberlyst-15 resin beads, Nafion particles), acidicly enriched functionalized silica gel (e.g., silica supported sulfonic and phosphoric acids), acidicly enriched zirconium oxide, acidicly enriched aluminosilicate zeolites, acidicly enriched aluminophosposilicate zeolites, and any combination thereof.

In certain embodiments of the present invention, the solid support particles are selected for additional properties, e.g., related to use of the final THC product, and include, for example, to avoid leaching.

In certain embodiments of the present invention, the solid support particles are selected based on the hydrolytic stability, e.g., related to the linker to the acid functionality. In particular embodiments, this results in a reduction of sensitivity to moisture.

In certain embodiments, the acidicly enriched solid support particles are renewable, i.e., may be used again, supporting a more renewable "green" process.

In certain embodiments of the present invention, the acidicly enriched solid support particles are support particles of an ion-exchange type, e.g., such as AMBERLYST-15 or 35 resins that are available in a bead form. These support particles are acidic, e.g., strongly acidic, ion exchange styrene-divinylbenzene polymeric scaffold containing sulfonic acid moieties (5-6 eqv/kg) and developed for binding of cationic impurities in chromatography, purification and other applications. In light of the instant discovery, and without wishing to be bound by theory, it is believed that the pore structure of AMBERLYST 15 and 35 permits ready access of reactants to the hydrogen ion sites located throughout the bead, thus facilitating successful performance even in non-swelling organic media.

In certain embodiments of the present invention, the acidicly enriched solid support particles are support particles of an active ion-exchange acidic catalyst, such as Nafion-H®, a sulfonated polymer prepared by polymerization of perfluorinated vinyls and perfluorinated vinyl esters, tetrafluoro-ethylene-perfluoro-3,6-dioxa-4-methyl-7-octensulfonic acid. Without wishing to be bound by theory, it is believed its superacidity is attributed to the electron-withdrawing effect of the perfluoroalkyl backbone to which the sulfonic acid group is attached. Mechanistic studies of various transformations show that the acidity of Nafion-H under the reaction conditions is comparable to that of 96-100% $H_2SO_4$. Nafion-H® has relatively high working temperatures as compared to other polymers and is stable up to a temperature of 210° C. It is an eco-friendly and recyclable catalyst due to the added advantages of its inertness to corrosive environments, ease of recovery and recyclable nature. The catalytic activation of Nafion-H® resin utilizes polar solvents due to increased swelling, which leads to better accessibility of the sulfonic acid active sites.

In certain embodiments of the present invention, the acidicly enriched solid support particles are support particles of a Lewis acid, e.g., such as silica-bound $BF_3$ catalyst that is believed to contain as active catalytic centers —$OBF_2$ and —O—B(F)—O— species (Oshidome, 2001).

In certain embodiments of the present invention, the acidicly enriched solid support particles are support particles of an oxide, e.g., such as those with propyl sulfonic and tosyl sulfonic acid incorporated into the amorphous silica network.

In certain embodiments of the present invention, the acidicly enriched solid support particles are support particles of aluminosilicates or aluminophosposilicates.

III. Devices of the Invention

The methods of the present invention may be utilized for the production of THC in certain devices through the conversion from CBD. As such, in certain embodiments, the devices of the present invention will be designed to operate in accordance with the methods of the present invention as described herein. In this way, the devices of the present invention comprise a vessel for containing acidicly enriched solid support particles, and a plurality of CBD-activated acidicly enriched solid support particles positioned inside the vessel.

The devices of the present invention are well suited for use in commercial THC production or for personal THC production, and for both medical and recreational purposes. In certain embodiments of the present invention, the device is for medical application, e.g., with medical precision.

A. Production Device

One embodiment of the present invention provides a tetrahydrocannabinol (THC) production device comprising:
 a vessel for containing acidicly enriched solid support particles; and
 a plurality of CBD-activated acidicly enriched solid support particles positioned inside the vessel, wherein THC is produced from the CBD-activated acidicly enriched solid support particles.

Another embodiment of the present invention provides a tunable tetrahydrocannabinol (THC) production device comprising:
 a vessel for containing acidicly enriched solid support particles; and
 a plurality of acidicly enriched solid support particles positioned inside the vessel, wherein THC is produced from the CBD-activated acidicly enriched solid support particles.

In certain embodiments of the THC production devices of the present invention are tunable, where the THC may be selectively produced in the accelerated conversion environment. In certain embodiments, the selectivity is the result of selecting the acidicly enriched solid support particles, selecting temperature, selecting time of reaction before extraction, selecting a particular solvent, or any combination thereof. In particular embodiments, the selectively is produced as a single product or ratio of multiple products, e.g., including starting material CBD.

In certain embodiments of the tetrahydrocannabinol (THC) production devices of the present invention, the vessel is selected from the group consisting of a reaction vessel, a collection vessel, a column, a vape device, a cartridge for a vape device, a smoking device, a skin applicator, a syringe, an oral delivery device, a sublingual delivery device, and any combination thereof. In a particular embodiment, the vessel is selected based upon the desired use, delivery, or application, e.g., commercial production or personal use. In certain embodiments, the present invention provides methods of producing these device by introducing the CBD to a precursor device, i.e., a device prior to the introduction of CBD.

In certain embodiments of the THC production devices of the present invention, the vessel is selected for commercial production of THC In certain embodiments of the THC production devices of the present invention, the vessel is selected for personal use production of THC. In certain embodiments, the personal use production of THC is a medical device, e.g., with medical precision control over the ratio of THC-9 and THC-8.

In certain embodiments of the THC production devices of the present invention, the device is programmed with a time controller to select the ratio of THC-9 and THC-8.

i. Commercial Application

In certain embodiments of the THC production devices of the present invention, the THC production device further comprises a heating source suitable to control the temperature of vessel.

In certain embodiments of the THC production devices of the present invention, the heating source is a heating jacket.

In certain embodiments of the THC production devices of the present invention, the THC production device further comprises a means for extraction of the THC from the acidicly enriched solid support particles in the vessel.

In certain embodiments of the THC production devices of the present invention, the solid support particles are selected from the group consisting of acidicly enriched resin beads (e.g., Amberlyst-15 resin beads, Nafion particles), acidicly enriched functionalized silica gel (e.g., silica supported sulfonic and phosphoric acids), acidicly enriched zirconium oxide, acidicly enriched aluminosilicate zeolites, acidicly enriched aluminophosposilicate zeolites, and any combination thereof.

In certain embodiments of the THC production devices of the present invention, the THC produced in the accelerated conversion environment is selected from the group consisting of THC-9, THC-8, and any combination thereof.

In certain embodiments of the THC production devices of the present invention, 500 g or greater of THC may be produced in a single use of the device (e.g., 1 kg or greater, e.g., 5 kg or greater, e.g., 10 kg or greater, e.g., 20 kg or greater, e.g., 100 kg or greater, e.g., 500 kg or greater.

In certain embodiments of the THC production devices of the present invention, the THC is produced with enhanced conversion efficiency of the CBD with greater than 75% efficiency (e.g., greater than 80% efficiency, e.g., greater than 85% efficiency, e.g., greater than 90% efficiency, e.g., greater than 95% efficiency).

In certain embodiments of the THC production devices of the present invention, the THC produced (e.g., crude) is greater than 80% pure (e.g., greater than 85% pure, e.g., greater than 90% pure, e.g., greater than 95% pure).

In certain embodiments of the THC production devices of the present invention, the THC is produced at an enhanced rate (e.g., less than or equal to 3 hours, e.g., less than or equal to 2 hours, e.g. less than or equal to 1 hour, e.g., less than or equal to 45 min, e.g., less than or equal to 30 min, e.g., less than or equal to 20 min, e.g., less than or equal to 15 min, e.g., less than or equal to 10 min, e.g., less than or equal to 5 min).

In certain embodiments of the THC production devices of the present invention, the vessel comprises a first column.

In certain embodiments of the THC production devices of the present invention, the device further comprises a second vessel (e.g., for a multi-column device).

In certain embodiments of the THC production devices of the present invention, the THC production device further comprises at least one additional column comprising a second plurality of acidicly enriched solid support particles different from the first column.

ii. Personal Use

Another embodiment of the present invention provides a tetrahydrocannabinol (THC) production personal use device for use in producing amounts of THC that would be for on-demand use, e.g., single administration use. In certain embodiments, the vessel size is selected given the desire to deliver a limited amount of THC doses for personal use.

Another embodiment of the present invention provides a tetrahydrocannabinol (THC) production personal use device comprising
 a vessel for containing acidicly enriched solid support particles, wherein the vessel is designed for personal use; and
 a plurality of acidicly enriched solid support particles positioned inside the vessel, wherein THC is produced from the CBD-activated acidicly enriched solid support particles.

In certain embodiments of the THC production personal use devices of the present invention, the vessel is a vaping device.

In certain embodiments of the THC production personal use devices of the present invention, the vessel is an oral delivery device.

In certain embodiments of the THC production personal use devices of the present invention, the vessel is a sublingual delivery device.

In certain embodiments of the THC production personal use devices of the present invention, the vessel comprises an extraction means to extract the THC from the acidicly enriched solid support particles, e.g., to filter THC from catalyst and/or to stop the conversion reaction.

In certain embodiments of the THC production personal use devices of the present invention, the device is tunable to selectively produce THC. In certain embodiments, the device is programmed with a selected reaction time to selectively produce THC. In particular embodiments, the reaction time is between 1 min and 10 min, e.g., 1 min and 5 min.

In certain embodiments of the THC production personal use devices of the present invention, the device is suitable for medical precision dosing of THC.

EXEMPLIFICATION

Having thus described the invention in general terms, reference will now be made to exemplary embodiments, and the accompanying drawings of exemplary embodiments, which are not necessarily drawn to scale, and which are not intended to be limiting in any way.

In this respect, it is to be understood that the invention is not limited in its application to the details of construction and to the arrangements of the components set forth in the following description or illustrated in the Figures. The invention is capable of other embodiments and of being practiced and carried out in various ways. Also, it is to be understood that the phraseology and terminology employed herein are for the purpose of description and should not be regarded as limiting.

The present invention has identified that the conversion of CBD to THC may be effectively catalyzed by Lewis and BrØnsted acidic catalysts on the solid support (i.e., acidicly enriched solid support particles) with multiple advantages over the known solution chemistry. The catalytic conversions of CBD and THC may be represented as follows in Scheme 1:

Scheme 1

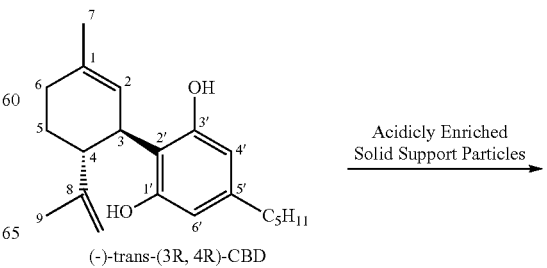

(-)-trans-(3R, 4R)-CBD

Acidicly Enriched Solid Support Particles

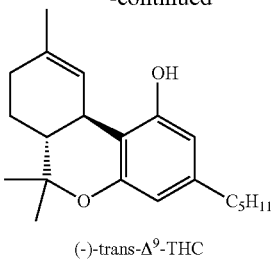

(-)-trans-Δ⁹-THC

+

(-)-trans-Δ⁸-THC

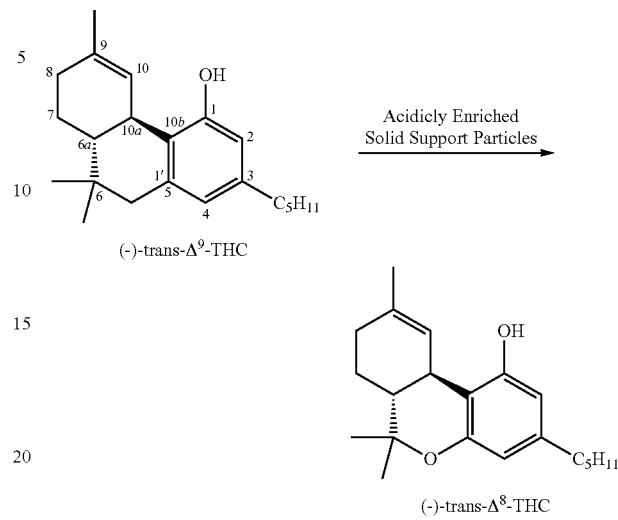

Scheme 2

(-)-trans-Δ⁹-THC

→ Acidicly Enriched Solid Support Particles (-)-trans-Δ⁸-THC

Representative catalysts from certain main groups of acidicly enriched solid support particles known in the art, namely, (i) ion-exchange resins, (ii) silica and alumina oxides and (iii) aluminosilicates (zeolites) were tested (Table 1). Moreover, the functionality shown in Table 1 describes the functional groups covalently bound to the solid support particles that result in the acidic enrichment, i.e., creation of acidity, of the acidicly enriched solid support particles

TABLE 1

Representative BrØnsted and Lewis acidicly enriched solid support particles.

| Solid Acid | Type | Core Framework | Acid Type | Functionality |
|---|---|---|---|---|
| Amberlyst | Ion-exchange resin | Organic-Polystyrene | BrØnsted | Toluene Sulfonic |
| Nafion | Ion-exchange resin | Organic-Tetrafluoroethylene | BrØnsted | Fluoroalkyl sulfonic |
| $Al_2O_3/SO_3H$ | Oxide | Inorganic-$Al_2O_3$ | BrØnsted | Sulfonic |
| $SiO_2/H_3PO_4$ | Oxide | Inorganic-$SiO_2$ | BrØnsted | Phosphoric |
| $SiO_2/SO_3H$ | Oxide | Inorganic-$SiO_2$ | BrØnsted | Alkyl-, aryl-sulfonic |
| $ZrO_2/H_2SO_4$ | Oxide | Inorganic-$ZrO_2$ | Lewis/BrØnsted | Sulfonic, metal sites |
| $BF_3/SiO_2$ | Oxide | Inorganic-$SiO_2$ | Lewis | —$OBF_2$ |
| Zeolites | Aluminophospho-silicate | Inorganic-$SiO_2/Al_2O_3/PO_4$ | Lewis/BrØnsted | —OH, metal sites |
| Zeolites | Aluminosilicate | Inorganic-$SiO_2/Al_2O_3$ | Lewis/BrØnsted | —OH, metal sites |

The acidicly enriched solid support particles described above and in specific examples below were obtained from commercial sources and used in the catalytic conversions described herein. However, the choice of catalyst materials is not limited and may be, in certain embodiments, expanded to other various compositions summarized in Table 1 and based both on organic and inorganic scaffolds. Appropriate selection and design of such catalysts to fine-tune their technical performance (in terms of conversion, selectivity, activity, stability etc.) and overall economics is within the skill of the ordinarily skilled artisan and therefore within the scope of the present invention in light of the disclosure presented herewith.

In certain embodiments, the THC-9 may be converted into THC-9 in accordance with Scheme 2.

Example 1

Conversion of CBD to (−)-Δ⁸-THC Using Ambersylt-15 Resin 50 mg of CBD powder (CBDistillery, Denver, Colo., >99% purity) was dissolved in 2 ml of heptane to which 10 mg of Amberlyst-15 resin beads (dry, H⁺ form, Dow Chemical Company; Acros Organics, Cat. No. AC202145000) have been added. The reaction mixture was refluxed in a round-bottom flask equipped with a condenser for 1 h, the catalyst beads were separated by filtration and the solvent removed in the rotovap. The HPLC of the reaction product revealed complete consumption of the starting CBD and formation of (−)Δ⁸-THC in 85% yield. The identity of the product was confirmed by LC-MS spectroscopy (M+H⁺, 314.4), HPLC (using a standard sample of (−)-Δ⁸-THC from Restek Corporation that displayed an identical to the reaction product retention time of 8.1 min; see HPLC method details below; FIG. 1), and by ¹H NMR (following the analysis as reported by Choi et al., 2004 and Taylor et al., 1966)—the assignment to Δ⁸-position of the vinyl group (compared to Δ⁹-) was confirmed by the upfield shift from 6.3 to 5.4 ppm and the trans-configuration of the H-10/H-6 protons by a related coupling constant of 10.8 Hz (observable for the H-10 proton at 2.7 ppm).

The HPLC Setup:

Agilent 1100 setup with a diode array detector, detection wavelength λ=228 nm, column Agilent Eclipse XD-8 Phenyl, 4.6×150 mm, 5 micron. Mobile phase A-0.1% formic acid in water; mobile phase B-0.1% formic acid in acetonitrile; flow rate 1.15 ml/min, injection volume 10 microL. HPLC method details: 72% B (0 min) to 81% B (4.5 min), to 100% B (9 min), to 72% B (10 min). A typical HPLC trace of the reaction mixture is shown in the FIG. 1.

$^1$H NMR (400 MHz, CDCl$_3$): 0.88 (3H, t, 7.1 Hz) 5''-Me; 1.10 (3H, s) 9-Me; 1.32 (4H, m) 3'', 4$^8$-CH$_2$; 1.38 (3H, s) 8-Me; 1.56 (2H, q, 7.6 Hz) 2''-CH$_2$; 1.70 (3H, s) 3-Me; 1.80 (m) 6-H; 2.13 (1H, m), 1.64 (1H, s) 5-CH$_2$; 2.13 (1H, m) 5-H; 2.44 (2H, td, 8.3 Hz, 2.1 Hz) 1''-CH$_2$; 2.70 (1H, td, 10.8 Hz, 4.8 Hz) 1-H; 3.24 (2H, dd, 16.5 Hz, 3.7 Hz) 2-CH$_2$; 5.43 (1H, brd, 4.8 Hz) 4-CH$_2$; 6.11 (1H, d, 1.6 Hz) 3'-H; 6.27 (1H, d, 1.5 Hz) 5'-H.

The reaction had similar outcomes regarding the product yield and purity when conducted in hexane (at reflux), isopropyl myristate (IMS) at 100° C. and medium chain triglycerides (100° C., 10 h). The higher reaction temperature was not found a prerequisite for completion in hexane or heptane with a full conversion also achieved in 48 h at ambient temperature. The reaction temperatures above 100° C. lead to rapid accumulation of the degradation products.

Reaction proceeded only partially in alcohol—after 2 h at reflux in isopropyl alcohol only ca. 10% of CBD was consumed and produced a mixture of (−)Δ$^8$-THC and (−)Δ$^9$-THC.

A full catalytic conversion of CBD to (−)-Δ$^8$-THC (78%) also took place by heating a commercial CBD isolate containing minor quantities of other cannabinoids and terpenes (CBDistillery, Denver, Colo., Full Spectrum Isolate, 250 mg CBD in 15 ml MCT coconut oil) for 10 h at 100° C.

In certain embodiments, the optimal amount of catalyst was found to be in the range of 5-25% w/w to CBD. By running the time course of the Amberlyst-catalyzed reaction at milder conditions (e.g., ambient temperature and refrigerating to 4° C.; T=1-336 h), intermittent formation of the (−)-trans-Δ$^9$-THC stereoisomer was observed (with shorter retention time, see FIG. 1), along with the residual unreacted fractions of the starting CBD.

In conclusion, the reaction proceeded in various non-protic solvents and oils and could be completed in light hydrocarbons at ambient temperatures in 2 days or in accelerate mode at higher temperatures in 1-10 h. The use of hydrocarbons makes it possible for direct utilization of the reaction mixture for additional purification using Centrifugal Partitioning Chromatography (CPC) in scale up preparations of THC (Hazecamp, 2004).

Example 2

Conversion of CBD to (−)-Δ$^8$-THC Using Nafion 50 mg of CBD was dissolved in 2 ml of heptane to which 10 mg of Nafion-SAC-13 (fluorosulfonic acid Nafion® polymer on amorphous silica, 10-20% load, 0.6 ml/g pore volume, >10 nm pore diameter, surface are >200 m$^2$/g) was added.

The reaction mixture was refluxed in a round-bottom flask equipped with a condenser for 1 h, the catalyst beads were separated by filtration and the solvent removed in the rotovap. The HPLC confirmed the formation of (−)-Δ$^8$-THC as a major reaction product in 66% yield.

Example 3

Conversion of CBD to (+Δ$^8$-THC Using Silica Supported BF$_3$ 50 mg of CBD was dissolved in 2 ml of heptane to which 10 mg of silica supported BF$_3$ catalyst (Sigma Aldrich, Cat. No. 718416) was added. The reaction mixture was refluxed in a round-bottom flask equipped with a condenser for 1 h, the catalyst particles were separated by filtration and the solvent removed in the rotovap. The HPLC of the reaction product confirmed the formation of (−)-Δ$^8$-THC as a major reaction product in 70% yield.

Example 4

Conversion of (−)Δ$^9$-THC to (−)Δ$^8$-THC 50 mg of (−)Δ$^9$-THC was dissolved in 2 ml of heptane to which 10 mg of Amberlyst catalyst was added. The reaction mixture was refluxed in a round-bottom flask equipped with a condenser for 2 h, the catalyst beads were separated by filtration and the solvent removed in the rotovap. The HPLC of the reaction product confirmed the formation of (−)Δ$^8$-THC (89% yield).

Example 5

Conversion of CBD to (−)-Δ$^8$-THC and (−)-Δ$^9$-THC Using Silica Supported Sulfonic Acids and Other Oxides 50 mg of CBD was dissolved in 2 ml of hexane to which 10 mg of SiliaBond Functionalized Silica Gel Propyl Sulfonic acid (SCX-2) or SiliaBond Tosic Acid (SCX) catalyst, both end-capped, particle size 40-60 micron, 0.6-0.8 mmol/g (SiliCycle, Quebec, Canada), were added. The reaction mixture was refluxed in a round-bottom flask equipped with a condenser for 5 min, the catalyst beads separated by filtration and the solvent removed in the rotovap. The HPLC of the reaction product confirmed the formation of (−)-Δ$^8$-THC (66% yield) for both SCX-2 and SCX catalysts.

The CBD conversion was also almost complete in no solvent conditions by heating the melt of CBD with 10% by weight of the catalyst at 100° C. for 5 min and recovering the product by extracting the melt with hexane.

The reaction was also followed by HPLC at ambient temperature for the SCX catalyst. Intermitted formation of both THC-8 and THC-9 was observed. Close to the completion point (6% residual CBD) at 90 min, there was 31% of THC-9 and 37% of THC-8 in the mixture (Table 2).

TABLE 2

Reaction Products of CBD-to-THC Conversion Catalyzed by Si-Sulfonic Acids

| Composition of reaction products | Reaction Conditions | | | | |
| --- | --- | --- | --- | --- | --- |
| | 10 min, RT, Hexane | 60 min, RT, Hexane | 90 min, RT, Hexane | 5 min, Reflux Hexane | 5 min, 100° C., Solid |
| CBD, % | 67 | 16 | 6 | 1 | 0 |
| THC-9, % | 20 | 35 | 31 | 4 | 3 |
| THC-8, % | 5 | 24 | 37 | 66 | 64 |

Silicagel catalysts provided a surprising overall acceleration of the CBD conversion (>10×) compared to Amberlyst, Nafion and $BF_3/SiO_2$. Also silicagels allowed substantial stabilization of the THC-9 isomer in a convenient adaptation of the reaction at room temperature. Three other tested solid catalysts showed intermittent formation THC-9 only at early reaction time points corresponding to very low conversion of CBD and thus bearing little practical utility as an approach to THC-9.

Other oxide type catalysts with different core and acid functionality were tested producing results that are summarized in Table 3. Moreover, the functionality shown in Table 3 describes the functional groups covalently bound to the solid support particles that result in the acidic enrichment, i.e., creation of BrØnsted acidity, of the acidicly enriched solid support particles.

TABLE 3

Oxide Type of Catalysts Tested

| Catalyst | Core | Vendor | Functionality | Catalytic Activity |
|---|---|---|---|---|
| SCX-2 | $SiO_2$ | Silicycle R51230B | Propylsulfonic Acid, end-capped silica | High |
| SCX | $SiO_2$ | Silicycle R60530B | Arylsulfonic Acid, non-capped silica | High |
| SCX, capped | $SiO_2$ | Silicycle R60430B | Arylsulfonic acid, end-capped silica | High |
| $ZrO_2 H_2SO_4$ | $ZrO_2$ | Alfa Aesar | Sulfuric Acid | Low (20% conversion, refluxed heptane, 0.5 h) |
| Phos-Cat1 | $SiO_2$ | Carbosynth | Phosphoric Acid | Medium (74% conversion, refluxed heptane, 1 h) |
| $Al_2O_3$ acidic | $Al_2O_3$ | Alfa Aesar | Al—OH | VERY LOW |
| $NaHSO_4$ | Hydrosulfate | Aldrich | $HSO_4^-$ | VERY LOW |

It is noteworthy that zirconium sulfuric acid, known to possess some superacidity properties, showed low activity along with somewhat more active phosphoric acid functionalized silica. In certain embodiments, the acidicly enriched solid support particles are not $Al_2O_3$ acidic or $NaHSO_4$. In certain embodiments, the acidicly enriched solid support particles are not $ZrO_2H_2SO_4$.

Example 6

Conversion of CBD to (−)-Δ$^8$-THC and (−)-Δ$^9$-THC Using Aluminosilicates

It was further discovered that some aluminosilicates and aluminophosposilicates act as very efficient catalysts of the CBD-to-THC conversion at loads of 10-50%. The tested materials are listed in Table 3. In these embodiments, it was essential to have the catalyst in the H+ form. When in the salt form (shown for Zeolite Y), the materials were found to be inactive.

TABLE 4

Aluminosilicate and Aluminophosphosilicate Tested for Catalytic CBD Conversion

| Catalyst | Si/Al Ratio | Largest Pore Size, Å | Activity |
|---|---|---|---|
| ZSM-5 | 15:1 | 10 | Low (7% conversion, 30 min reflux heptane) |

TABLE 4-continued

Aluminosilicate and Aluminophosphosilicate Tested for Catalytic CBD Conversion

| Catalyst | Si/Al Ratio | Largest Pore Size, Å | Activity |
|---|---|---|---|
| Zeolite Y | 5:1 | 12 | High |
| Zeolite Y (Na+) | 5:1 | 12 | Inactive |
| Zeolite Beta | 360:1 | 12 | High |
| SAPO-34 | 1:4 | 8 | Inactive |
| SAPO-11 | 1:8 | 10 | High |

In certain embodiments, the acidicly enriched solid support particles are not SAPO-34. In certain embodiments, the acidicly enriched solid support particles are not ZSM-5.

The reaction proceeds with high conversion outcomes in refluxed heptane over a period of 1 h. Surprisingly, the transformation is significantly accelerated when conducted in the melt, without any solvent. Using aluminosilicates helps to stabilize THC-9 vs. THC-8 reaction products. In only 5 minutes time, the conversion rate was already about 80% with THC-9/THC-8 ratio of 2:1. The outcomes of catalytic transformations in different reaction conditions for the most active materials, i.e., Zeolite Y, SAPO-11 and Zeolite Beta are summarized in the Tables 5-7.

TABLE 5

Reaction Products of CBD-to-THC Conversion Catalyzed by Aluminophosphosilicate SAPO-11

| Composition of Reaction Products | Reaction Conditions (Time, Temperature, Solvent) | | | | |
|---|---|---|---|---|---|
| | 5 min, Reflux Heptane | 30 min, Reflux Heptane | 60 min, Reflux Hexane | 5 min, Reflux Hexane | 5 min, 100° C., Solid |
| CBD, % | 72 | 27 | 2 | 20 | 2 |
| THC-9, % | 21 | 43 | 45 | 46 | 31 |
| THC-8, % | 2 | 14 | 23 | 22 | 35 |

TABLE 6

Reaction Products of CBD-to-THC Conversion
Catalyzed by Aluminosilicate Zeolite Y

| Composition of Reaction Products | Reaction Conditions (Time, Temperature, Solvent) | | | | |
|---|---|---|---|---|---|
| | 5 min, Reflux Heptane | 60 min, Reflux Heptane | 5 min, 100° C., Solid | 15 min, 100° C., Solid | 30 min, 100° C., Solid |
| CBD, % | 68 | 8 | 19 | 4 | 1 |
| THC-9, % | 22 | 47 | 47 | 42 | 36 |
| THC-8, % | 2 | 23 | 23 | 36 | 44 |

TABLE 7

Reaction Products of CBD-to-THC Conversion
Catalyzed by Aluminosilicate Zeolite Beta

| Composition of Reaction Products | Reaction Conditions (Time, Temperature, Solvent) | | | |
|---|---|---|---|---|
| | 5 min, Refl. Heptane | 60 min, Refl. Heptane | 5 min, 100° C., Solid | 15 min, 100° C., Solid |
| CBD, % | 55 | 12 | 64 | 53 |
| THC-9, % | 27 | 49 | 22 | 27 |
| THC-8, % | 3 | 12 | 2 | 3 |

REFERENCES

1. Y. Gaoni and R. Mecholaum, Isolation, Structure, and Partial Synthesis of an Active Constituent of Hashish, *J. Am. Chem, Soc.*, 1964. Vol. 86, pp. 1646-1647.
2. Y. Gaoni and R. Mecholaum, Hashish-VII. The Isomerization of Cannabidiol to Tetrahydrocannabinols, *Tetrahedron*, 1966. Vol. 22, pp. 1481-1488.
3. Y. Gaoni, R. Mecholaum, Concerning the Isomerization of delta-1 to delta-6-tetrahydrocannabinol. *J. Am. Chem. Soc.*, 1966, Vol. 88, pp. 5673-5675.
4. G. R. B. Webster, L. P. Sarna, R. Mecholaum, Conversion of CBD to Delta8-THC and Delta9-THC, U.S. patent application Ser. No. 10/469,928.
5. M. Kidwai, R. Chauhan and S. Bhatnagar, Nafion-H: A Versatile Catalyst for Organic Synthesis, *Current Organic Chemistry*, 2015, 19, pp. 72-98.
6. R. J. Razdan, H. C. Dalzell, G. R. Handrick, Hashish, A Simple One-Step Synthesis of (−)-deltal-Tetracannabinol (THC) from p-Mentha-2,8-dien-1-ol and Olivetol, *J. Am. Chem. Soc.* 1974, Vol. 96, pp. 5860-5866.
7. P. Gupta, S. Paul, Solid Acids: Green Alternatives for Acid Catalysis, *Catalysis Today*, 2014, Part B, Vol. 236, pp. 153-214.
8. L. Hanus, S. M. Meyer, E. Munoz, O. Taglialatela-Scafatid and G. Appendino, Phytocannabinoids: a Unified Critical Inventory, *Nat. Prod. Rep.*, 2016, Vol. 33(12), pp. 1357-1392.
9. L. E. Hollister, Structure-Activity Relationships in Man of *Cannabis* Constituents and Homologs and Metabolites of delta-9-Tetrahydrocannabinol, *Pharmacology*, 1974, Vol. 11, pp. 3-11.
10. Y. H. Choi, A. Hazelkamp, A. M. G. Peltenburg-Looman, M. Frederich, C. Erkelens, A. W. M. Lefebr, R. Verpoorte, NMR. Assignments of the Major Cannabinoids and Cannabiflavonoids Isolated from Flowers of *Cannabis sativa*, *Phytochem. Anal.* 2004, Vol. 15, pp. 545-354.
11. E. C. Taylor, K. Lenard, Y. Shvo, Active Constituents of Hashish. Synthesis of dl-$\Delta^6$-3,4-trans-Terahydrocannabinol, *J. Am. Chem. Soc.*, 1966, pp. 367-370.
12. T. Y. Oshidome, Z. D. Ang, and B. A. Morrow, Infrared Spectra of Silica Reacted with Gaseous $BF_3$ and Analyses of the Reaction, *Anal. Sc.* 2001, Vol. 17 Suppl., pp. i1085-1088.
13. Hazekamp, R. Simons, A. Peltenburg-Looman, M. Sengers, R. van Zweden, R. Verpoorte, Preparative Isolation of Cannabinoids from *Cannabis sativa* by Centrifugal Partition Chromatography, *J. Liq. Chrom. & Rel. Technol.* 2004, Vol. 27, pp. 2421-2439.
14. H. Y. Luo, J. D. Lewis, and Y. Roman-Leshkov, Lewis Acid Zeolites for Biomass Conversion: Perspectives and Challenges on Reactivity, Synthesis, and Stability, *Ann. Rev. Chem. Biochem. Eng.*, 2016.
15. R. H. Vekariya and H. D. Patel, Alumina Sulfuric Acid (ASA), Tungstate Sulfuric Acid (TSA), Molybdate Sulfuric acid (MSA) and Xanthan Sulfuric Acid (XSA) as Solid and Heterogeneous Catalysts in Green Organic Synthesis: a Review, ARKIVOC, 2016, pp. 70-96.
16. H. Sharghi, M. H. Sarvari and R. Eskandari, Alumina Sulfuric Acid as a Novel Heterogeneous System for Esterification of Carboxylic Acids in Solvent Free Conditions, *J. Chem. Res.*, 2005, pp. 488-491
17. A. D. Sawant, D. G. Raut, A. R. Deorukhkar, U. V. Desai, M. M. Salunkhe, Silica supported orthophosphoric acid ($H_3PO_4.SiO_2$): a green, heterogeneous catalyst for solvent-free oxathioacetalization of aldehydes, *Green Chem. Let. Rev.*, 2011, Vol. 4, No. 3, pp. 235-240.
18. X. Zhang, Y. Zhao, S. Xu, Y. Yang, J. Liu, Y. Wei, Q Yang, Polystyrene Sulphonic Acid Resins with Enhanced Acid Strength via Macromolecular Self-Assembly within Confined Nanospace, *Nature Com.*, 2014.
19. P. Wang, Y. Zhao, J. Liu, Versatile Design and Synthesis of Mesoporous Sulfonic Acid Catalysts, *Sc. Bull.* 2018, 63, pp. 252-266.
20. Zhou J, Wang Y, Guo X, et al. Etherification of Glycerol with Isobutene on Sulfonated Graphene: Reaction and Separation. *Green Chem.* 2014, Vol. 16, pp. 4669-79.

INCORPORATION BY REFERENCE

The entire contents of all patents, published patent applications and other references cited herein are hereby expressly incorporated herein in their entireties by reference.

EQUIVALENTS

Those skilled in the art will recognize, or be able to ascertain using no more than routine experimentation, numerous equivalents to the specific procedures described herein. Such equivalents were considered to be within the scope of this invention and are covered by the following claims. Moreover, any numerical or alphabetical ranges provided herein are intended to include both the upper and lower value of those ranges. In addition, any listing or grouping is intended, at least in one embodiment, to represent a shorthand or convenient manner of listing independent embodiments; as such, each member of the list should be considered a separate embodiment.

What is claimed is:

1. A material-efficient method for conversion of cannabidiol (CBD) to tetrahydrocannabinol (THC) comprising the step of:
   introducing CBD to acidicly enriched solid support particles to create a CBD-activated accelerated conversion environment, such that THC is produced.

2. The material-efficient method of claim 1, wherein the solid support particles are selected from the group consisting of acidicly enriched resin beads, acidicly enriched functionalized silica gel, acidicly enriched zirconium oxide, acidicly enriched aluminosilicate zeolites, acidicly enriched aluminophosposilicate zeolites, and any combination thereof.

3. The material-efficient method of claim 1, further comprising the step of heating said CBD-activated accelerated conversion environment.

4. The material-efficient method of claim 3, wherein the accelerated conversion environment is heated to less than or equal to 100° C.

5. The material-efficient method of claim 1, wherein the step of introducing the CBD to the acidicly enriched solid support particles is through solvent dissolution of the CBD to create the CBD-activated accelerated conversion environment.

6. The material-efficient method of claim 1, wherein the step of introducing the CBD to the acidicly enriched solid support particles is through solvent-free direct melt of the CBD to create the CBD-activated accelerated conversion environment.

7. The material-efficient method of claim 1, further comprising the step of extraction of the solid support particles.

8. The material-efficient method of claim 1, wherein the THC produced in the accelerated conversion environment is selected from the group consisting of THC-9, THC-8, and any combination thereof.

9. The material-efficient method of claim 8, wherein the THC is selectively produced in the accelerated conversion environment.

10. The material-efficient method of claim 8, wherein the THC produced in the accelerated conversion environment has a THC-9 bias.

11. The material-efficient method of claim 8, wherein the THC produced in the accelerated conversion environment has a THC-8 bias.

12. A solvent-free method for conversion of cannabidiol (CBD) to tetrahydrocannabinol (THC) comprising the step of:

introducing CBD to acidicly enriched solid support particles through direct melt of the CBD to create a CBD-activated accelerated conversion environment, such that THC is produced.

13. A tetrahydrocannabinol (THC) production device comprising:

a vessel for containing acidicly enriched solid support particles; and a plurality of CBD-activated acidicly enriched solid support particles positioned inside the vessel, wherein THC is produced from the CBD-activated acidicly enriched solid support particles.

14. The THC production device of claim 13, wherein the vessel is selected from the group consisting of a reaction vessel, a collection vessel, a column, a vape device, a cartridge for a vape device, a smoking device, a skin applicator, a syringe, and any combination thereof.

15. The THC production device of claim 13, wherein the vessel is selected for commercial production of THC.

16. The THC production device of claim 13, wherein the vessel is selected for personal use production of THC.

17. The THC production device of claim 13, further comprising a heating source suitable to control the temperature of vessel.

18. The THC production device of claim 13, wherein the solid support particles are selected from the group consisting of acidicly enriched resin beads, acidicly enriched functionalized silica gel, acidicly enriched zirconium oxide, acidicly enriched aluminosilicate zeolites, acidicly enriched aluminophosposilicate zeolites, and any combination thereof.

19. The THC production device of claim 13, wherein the THC is produced in an accelerated conversion environment is selected from the group consisting of THC-9, THC-8, and any combination thereof.

20. The THC production device of claim 13 wherein the THC may be selectively produced in an accelerated conversion environment.

* * * * *